United States Patent [19]

Brundin

[11] Patent Number: 4,509,504
[45] Date of Patent: Apr. 9, 1985

[54] OCCLUSION OF BODY CHANNELS

[75] Inventor: Jan-Olof Brundin, Lidingö, Sweden

[73] Assignee: Medline AB, Stockholm, Sweden

[21] Appl. No.: 79,951

[22] Filed: Sep. 28, 1979

Related U.S. Application Data

[63] Continuation-in-part of Ser. No. 870,595, Jan. 18, 1978, abandoned.

[51] Int. Cl.³ .............................................. A61B 17/00
[52] U.S. Cl. .................................... 128/1 R; 128/130; 604/55
[58] Field of Search ............... 128/325, 130, 131, 341, 128/138 R, 1 R, 285, 294; 604/55

[56] References Cited

U.S. PATENT DOCUMENTS

| | | |
|---|---|---|
| 3,042,030 | 7/1962 | Read . |
| 3,230,953 | 1/1966 | Birnberg et al. ............ 128/130 |
| 3,675,639 | 7/1972 | Cimber ....................... 128/1 R |
| 3,690,316 | 9/1972 | Haller . |
| 3,818,894 | 6/1974 | Wichterle et al. ........... 128/1 R |
| 3,858,571 | 1/1975 | Rudolph ..................... 128/131 X |
| 3,867,329 | 2/1975 | Halpern et al. .............. 128/341 X |
| 3,943,045 | 3/1976 | Cordrey et al. .............. 525/426 |
| 3,957,362 | 5/1976 | Mancini et al. .............. 526/229 X |
| 4,030,504 | 6/1977 | Doyle ......................... 128/325 |
| 4,185,618 | 1/1980 | Corey ......................... 128/130 X |

Primary Examiner—Michael H. Thaler

[57] ABSTRACT

A method for obstructing channels, ducts and other hollow spaces in human and animal bodies is disclosed comprising inserting a device having a portion thereof adapted to swell at least 20% in size when in contact with the fluid of the human or animal body, the device being in a shape matching and cooperating with the channel to be obstructed.

12 Claims, 6 Drawing Figures

OCCLUSION OF BODY CHANNELS

CROSS-REFERENCE TO RELATED APPLICATIONS

This is a continuation-in-part of my earlier application Ser. No. 870,595 filed Jan. 18, 1978, now abandoned.

BACKGROUND OF THE INVENTION

The present invention relates to a device for temporary or permanent occlusion of channels or hollow spaces in human or animal bodies, particularly oviducts and spermatic ducts. The invention also includes a method of occluding a body reproduction channel by inserting a device of the type herein described.

Human and animal bodies contain a vast number of channels or vessels, through which fluid and/or other substances or objects can pass or be transported. In certain cases, it is desirable to disrupt such a passage. As an example, for contraceptive purposes the spermatic ducts and the oviducts or fallopian tubes can thus be occluded such that by the passage of sperms and ova, respectively, are prevented. In certain vascular diseases, for instance, it may be desired to stop the flow of blood through certain blood vessels. This is possible both on the arterial and veinous side of the circulatory system. Methods previously used for this purpose have had disadvantages such as, for instance, that the passage through the channel has been difficult to occlude completely, difficulty in reopening, when desired, and the like.

DETAILED DESCRIPTION OF THE INVENTION

It has now been found that these and other disadvantages can be eliminated by using a device consisting of a material, which when contacted with a body fluid, such as physiological fluids and blood, swells at least 20% in volume. Apart from this swelling, the device introduced must be substantially completely inert to the body fluids and to other surrounding body tissues. The amount of swelling of the device in contact with the body fluid is preferably at least 40%, more preferably at least 80% and may well be in the range between 20 and 300% depending on the swellable material employed, amount of fluid to which the device is exposed and the like. The channels in human beings and animals, which can be occluded by this device include blood vessels, urethers, spermatic ducts and oviducts as examples.

As used herein the dry state of the device means the condition of the device prior to contact with physiological fluids. It will be appreciated that the device itself may contain molecules of water trapped within a gel-like framework of polymeric bonds. This state is also referred to herein as non-hydrated. When contacted with the body fluids the device will become hydrated and swell to the extent indicated below.

The exact geometric form of the device is not critical and is conveniently essentially cylindrical, spherical or egg-shaped or may take the form of a teardrop. In certain instances the devices is preferably in the form of an hour-glass. However, generally the device will have a circular cross-section in that portion corresponding to and cooperating with that portion of the channel to be occluded. This cross-section of the device when in the dry state is preferably smaller than the cross-section of the channel to be occluded such that the device can conveniently be introduced along the channel and accurately positioned well before swelling is complete.

The device according to the invention is particularly suited for use as a contraceptive device and this is especially adapted for practicing a contraceptive method. According to this aspect of my invention the device is inserted into and positioned within the appropriate location in the spermatic ducts or the oviducts. The device is in this case preferably provided with an attached thread or string in such a way that it can be conveniently withdrawn usually without a surgical incision. This thread can be made of an X-ray opaque material enabling the physician to localize and determine the position of the device within the duct. The device itself can also contain X-ray contrast substances or materials which are themselves known.

When in contact with the fluid of the human or animal into which the device is inserted, the material of the device swells at least 20%, preferably at least 40%, more preferably at least 80%, and may even swell as much as 300%. In other respects, the material should be essentially inert and harmless to the body fluid and surrounding tissues and should remain intact, that is, should not be absorbed by the human or animal body into which the device is inserted. Suitable materials for this purpose are hydrogels, i.e. water-containing gels. Preferred hydrogels are polymers and copolymers of the acrylic type such as cross-linked polyacrylamide and polymers and copolymers of acrylic and methacrylic esters having at least one hydroxy radical in the side chain. A preferred monomer is 2-hydroxy-ethyl-methacrylate; other preferred monomers are monomethaylic esters of di- or triethylene glycol of 2,3-dihydroxypropane. As cross-linking agents polyfunctional acrylates, such as the esters of the same glycols, e.g. ethylene glycol-bis-methacrylate, are useful. Materials useful in accordance with the present invention as well as a process for their preparation are described in the U.S. Pat. No. 3,943,045 issued Mar. 9, 1976, the disclosure of which is hereby incorporated by reference.

The device in the dry state should be essentially elastic and plastic only to a very small extent. In its unswollen or non-hydrated state it may be rigid, stiff or hard, but should preferably soften upon swelling. The device can contain a reinforcing material, an armouring material if desired.

In use, the device according to the invention in the unswollen state, is introduced into a body channel, i.e. a natural or pathological hollow communication in the human or animal body, which can also be described as a hollow space, and will thereafter swell, when in contact with the body fluid, either human or animal, so that the device which can pass through the channel when inserted, will swell and effectively engage the walls of the channel. Through the pressure then exerted by the channel walls on the device, it will be slightly compressed simultaneously with a possible expansion of the elastic walls of the channel and swelling of the device as well. In this way the device occludes the entire cross-section of the channel and prevents anything from passing through the channel while at the same time the device is firmly anchored in position.

After insertion into an oviduct and expansion, the passage of ova to the uterus and spermatozoa, respectively, upwards through the oviduct to the unfertilized ovum will be prevented. After occlusion of the spermatic duct the outward passage of the spermatozoa will be prevented and a good contraceptive action is achieved. If desired, the inserted bodies can be withdrawn by surgical procedure or, as is the case when inserted in an oviduct, by extraction through the uterus when the device is provided with an attached thread for extracting the device.

Thus according to the method aspect of my invention an intra-tubal device (ITD) of a hydrogel of the type described is inserted into the transsectional star-shaped channel and positioned in the intramural part of the oviduct. A hysteroscope is used to guide and follow the insertion procedure. The muscular wall of the tube is distensible and in cross-section becomes round shaped; this is clearly visible during hysteroscopy. Thus to fully occlude the luminal passage the intra-tubal device has an essentially round cross-section thereby maximizing the area over which the surface of the device is in contact. Upon contact with the body fluids the hydrogel swells causing elongation and further contact. Contact is also enhanced by the softness of the porous surface of the swollen, hydrated device.

In order to fully secure the exact position of the device, prevent early expulsion and retain it in the desired position, it is preferred to employ one or more anchoring means, sometimes in the form of protruding wings and preferably of a physiologically inert but essentially non-swellable material. This wing approach is especially preferred in that the swelling process of the hydrogel takes place after insertion of the device. This results in a reduction of the length of the free ends of the projecting wings which, in turn, minimizes the damage that could be expected by the wing ends on the tubal wall.

It has been found that the rate of expulsion of hydrogel-type intra-tubal devices is greatest shortly after insertion and that this rate decreases as a function of time, presumably as the hydrogel becomes fully hydrated and swells to occlude and be retained in the tube. The anchoring wings provide a means to retain the device in place upon insertion and continue to effectively function for a period of time until the hydrogel is substantially completely hydrated and swollen to its maximum obtainable size.

BRIEF DESCRIPTION OF THE DRAWINGS

The device according to the invention will now be described in more detail referring to an embodiment used as a contraceptive inserted in the fallopian tube. In the drawings.

DETAILED DESCRIPTION OF THE DRAWINGS

Figure 1:
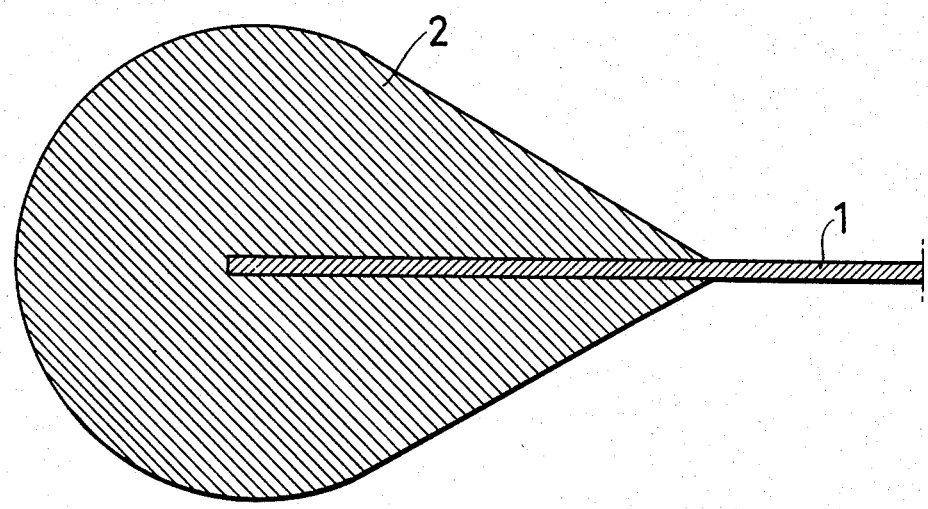
FIG. 1 is a sectional view of a preferred embodiment of the invention as a contraceptive device for insertion into the fallopian tube.

In FIG. 1 a thread 1 of nylon-6 is fastened to a body 2 of polyvinyl pyrrolidone by graft polymerizing vinyl pyrrolidone onto the thread. The body 2 is in the form of a drop. The diameter of the drop is approximately 0.8 mm in the unswollen, unhydrated state. In the swollen, fully hydrated state this diameter is approximately 1.45 mm.

Figure 2:
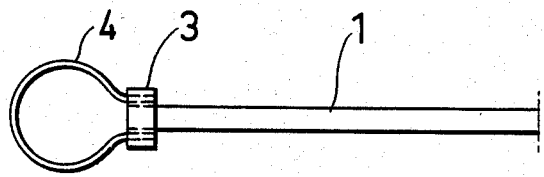
FIG. 2 is a partial view of FIG. 1.

FIG. 2 shows the thread 1 of the device according to FIG. 1. An X-ray opaque ring 3 is embedded in the end of the thread 1. Additionally, the thread end is provided with a loop 4, which also can be of an X-ray opaque material if desired, but is preferably part of the nylon thread itself in order to better secure the nylon thread to the body. The embodiment of FIG. 3 also contains a thread 1 of nylon embedded in a suitable length of the body 2 of hydrogel which is preferably polyvinyl pyrrolidone. In this embodiment the cross-section is circular and the hydrogel body 2 is to a length of about 7–11 mm, for instance, extended. The configuration of FIG. 3 can be used in the same way as the embodiment of FIG. 1 having about the same cross-sectional diameter.

Figure 3:
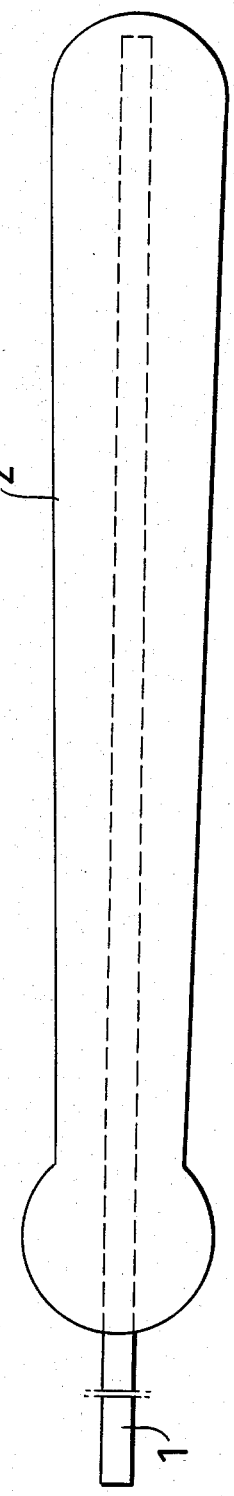
FIG. 3 is a view of another embodiment also useful as a contraceptive device for insertion into the fallopian tube.
Figure 5:
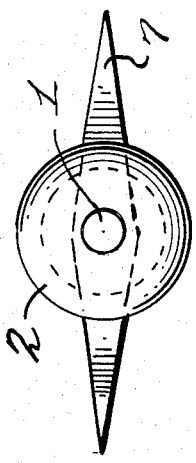
FIG. 5 is a perspective end view of FIG. 6.
Figure 6:
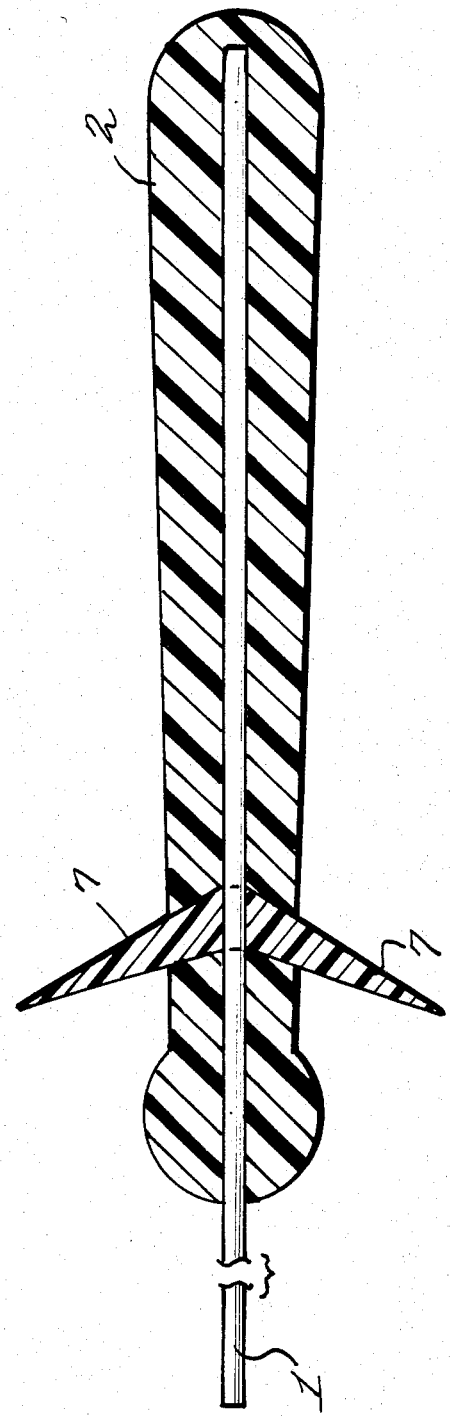
FIG. 6 is a sectional view of another preferred embodiment of the device of the present invention having anchoring wings for insertion into a fallopian tube and useful as a contraceptive device.

FIGS. 5 and 6 illustrate preferred embodiments of the invention similar to FIG. 3 in configuration having a hydrogel portion 2 of about 11 mm, a circular cross-section of about 1.6 mm tapering slightly to the bulbous end of about 1.4 mm. A nylon thread 1 is secured to the inner portion along the central axis of the hydrogel 2 and a pair of opposing nylon anchoring means in the form of wings 7 are secured to the nylon string 1 and extend in opposite directions. The anchoring wings 7 have a generally triangular shape when viewed from the end of the device as shown in FIG. 5 and are used to retain the device when implanted into the surrounding fallopian tube. It will be understood that one, two or several of such anchoring means may be used. Also differing shapes and configurations may be used as well, the specific shape and dimensions of the device of FIG. 1 being illustrative. The embodiment of FIGS. 5 and 6 may be fitted with an X-ray opaque ring and thread arrangement as shown in FIG. 2 or the hydrogel 2 may include an X-ray opaque material dispersed therein.

The body-cavity occluding portion of the device can preferably be made of a polymer of vinyl pyrrolidone and nylon in which liquid nylon or bulk nylon is polymerized with vinyl pyrrolidone, the nature of the reaction possibly being a graft polymerization or polymerization followed by cross-linking. The resulting material may be termed a hydrogel. This material behaves as comprising a skeleton made by hydrofobic material. Using such a material, the swelling and the water absorption power may be altered by changing the amounts of nylon and vinyl pyrrolidone to be polymerized. As an example, three (3) parts vinyl pyrrolidone and 1 part nylon forms a polymer having an expansion factor of 1.48, that is swells 48% in water, with a water content of 66%; five (5) parts vinyl pyrrolidone and 1 part nylon forms a polymer having an expansion factor of 1.78 with a water content of 78%. Other variations in monomer proportions will produce corresponding changes in the properties of the resulting hydrogel and are easily determined by the skilled worker. This embodiment comprising a skeleton (backbone) has an increased tenacity so that it easily can be withdrawn from the fallopian tube by means of the threads. This advantage is also obtained by a device containing a reinforcing material. However, the non-reinforced hydrogel having no backbone of hydrofobic material is not sufficiently tough, so that the withdrawal often fails by rupture of the device. The initial material is usually in the form of a viscous fluid which is injected into a mold of the desired configuration, as in FIGS. 1, 3 or 5, and copolymerized by gamma irradiation or heat.

Figure 4:
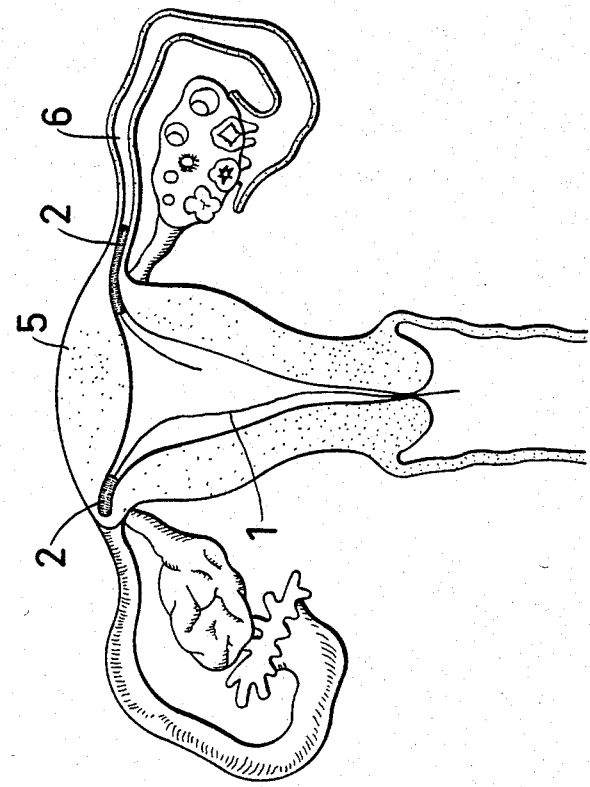
FIG. 4 is a schematic and partially sectional view of a uterus also showing the fallopian tube, the ovaries and part of the vagina.

FIG. 4 illustrates placement of a device according to the invention for use as a contraceptive in the oviducts. The device 2 is inserted from the uterus 5 through the openings of the oviducts 6 into the uterus. As shown in the figure, the body 2 is in contact with the walls of the oviducts 6 along the entire length of the device and follows completely and cooperates with the shape and motion of the oviduct. The device 2 to the left side of the drawing is provided with a long thread 1 so that it can be checked at the cervix uteri to confirm that the device still is in place.

My invention also includes a method for occluding the fallopian tubes by inserting a device of the type described into the appropriate position in the oviduct. A hysteroscope or similar device is employed in which each oviduct opening into the uterus is located and the device is implanted. Upon contact with the body fluids the hydrogel swells to a factor of from 20 to 80%, possibly up to 300% of its original size. The potential difficulty of expulsion of the device is substantially reduced or completely eliminated by the use of anchoring means of the type shown in FIG. 5. The hydrogel of the device, once inserted, swells over a period of time, typically in a week or so depending on the monomer mixing ratio and other factors, to its full, swollen size. Swelling force against the intramural wall is then maximized and the device is retained in place.

Using a device of the type described herein with anchoring means, an embodiment of which is illustrated in FIG. 5, several advantages are obtained. Firstly, with respect to manufacture, if the anchoring wings are nylon, preferably nylon-6, the anchoring wing can be used to attach to the retrieval thread 1 providing a more substantial bond as between the thread and the surrounding hydrogel. In the manufacturing process the gamma irradiation, as above described, causes the hydrogel to co-polymerize with the nylon-6 material of the anchoring wing. Secondary advantages are realized upon insertion of the anchoring-type device. The swelling process of the hydrogel occurs after insertion of the device which reduces the extent of protrusion of the anchoring wings by increasing the cross-sectional swelling of the hydrogel. This minimizes any damage caused by the wings to the tubal wall as the anchoring purpose of the wing or wings is gradually replaced by the swelling of the hydrogel of the device. The surface of the swollen hydrogel becomes porous and cooperates with the tubular wall in which the device is inserted.

It has been determined that intra-tubal devices of the type described are well tolerated by animal tissue. Devices of the type shown in FIG. 5 have been tested in paravertebral muscles of the rabbit and tissue reaction was compared to that of USP negative control plastic according to the procedure of Turner et al, J. Biomed. Mater Res. 7:39 (1973). Despite swelling of the hydrogel, which apparently exerted pressure upon the surrounding tissue, no severe tissue reaction was observed. The degree of tissue necrosis, inflammation, the invasion of polymorphs, eosinophils, macrophages, plasma cells, fibroblasts or edema produced by the hydrogel were not different from that produced by the USP negative plastic. Tests have also been conducted and except for disappearance of the thin intramural mucosa and a slight edema in the tubal wall, no pronounced damage was observed after a period of ten days. Follow-up studies and observations are continuing.

Even though the device according to the invention has been primarily described in the form of a contraceptive, it is understood that other medical applications of the device can be made, for instance, in the case of brain damage, such as cerebral haemorrhage, or when treating varicose veins. In such applications the device according to the invention is inserted in the appropriate vessel to completely obstruct that vessel. For certain circulatory applications an hour-glass form is preferred.

What is claimed is:

1. A method of occluding a body reproduction duct of an animal comprising the steps of
    (1) inserting a water-swellable contraceptive hydrogel article into said body reproduction duct;
    (2) bringing said hydrogel into contact with animal tissue fluid;
    (3) allowing said hydrogel to swell to an extent of at least 40% up to 300% of its original size and thereby
    (4) contacting and impinging upon the body duct in which said device is inserted,
    said device being substantially completely inert to said body fluid and the body tissue with which it is in contact, having a cross-sectional configuration corresponding to that of said reproduction duct and an indicator removal thread secured thereto.

2. The method according to claim 1 including the additional step of:
    (5) removing the thus-inserted hydrogel article.

3. The method according to claim 1 wherein said body reproduction duct is a fallopian tube and said article has a substantially circular cross-sectional configuration.

4. The method according to claim 3 wherein said article is in the form of a drop having a diameter of approximately 0.8 mm prior to swelling.

5. The method according to claim 3 wherein said article is substantially in the form of a cylinder slightly tapering towards the ends.

6. The method according to claim 1 wherein said hydrogel is a cross-linked, water-swellable copolymer of a hydrophilic hydrogel and nylon-6 as a hydrophobic monomer.

7. The method according to claim 1 or 6 wherein said device includes anchoring means to at least temporarily secure the device when implanted to said body reproduction duct.

8. The method according to claim 7 wherein said anchoring means includes a pair of fixed triangular shaped, pointed projections extending beyond the outer surface of the unswollen hydrogel prior to step (3).

9. The method according to claim 7 wherein said anchoring means is a pair of fixed, pointed projections of nylon-6 cross-linked to said hydrogel.

10. The method according to claim 1 wherein said device includes a visually observable removal thread one end being embedded into said hydrogel.

11. A method for at least temporarily occluding a reproductive oviduct or spermatic duct of an animal for contraceptive purposes, said method comprising the steps of:
    (a) forming a body of water-swellable polymeric hydrogel to the extent of at least 20% in volume by absorbing water, said hydrogel being substantially inert to body fluid and the tissue of said reproductive duct;
(b) shaping said hydrogel body into a cross-section which in the dry state is no larger than about the size of the cross-section of the reproductive duct;
(c) inserting the shaped hydrogel body in the dry state into the reproductive duct at a predetermined distance from the opening of the duct; and
(d) allowing the thus inserted shaped hydrogel body to remain in position, absorb water from the body fluid thereabout and anchoring itself by pressure against the surrounding walls of the duct.

12. The method according to claim 11 wherein said hydrogel swells to the extent of up to 300% and is substantially inert to both said fluid and the surrounding tissue of said duct.

* * * * *